United States Patent [19]

Iwane et al.

[11] Patent Number: 5,175,352

[45] Date of Patent: Dec. 29, 1992

[54] PROCESS FOR PREPARING 2,6-NAPHTHALENEDICARBOXYLIC ACID

[75] Inventors: Hiroshi Iwane; Takahiro Sugawara, both of Ibaraki, Japan

[73] Assignee: Mitsubishi Petrochemical Co., Ltd., Tokyo, Japan

[21] Appl. No.: 817,347

[22] Filed: Jan. 6, 1992

[30] Foreign Application Priority Data

Jan. 21, 1991 [JP] Japan .................................. 3-019191
Feb. 25, 1991 [JP] Japan .................................. 3-050087
Mar. 18, 1991 [JP] Japan .................................. 3-077233
Mar. 18, 1991 [JP] Japan .................................. 3-077234
Jun. 28, 1991 [JP] Japan .................................. 3-183860
Jun. 28, 1991 [JP] Japan .................................. 3-183861

[51] Int. Cl.⁵ ........................................... C07C 51/265
[52] U.S. Cl. .................................. 562/417; 562/487; 562/488
[58] Field of Search ................. 562/417, 487, 488

[56] References Cited

U.S. PATENT DOCUMENTS 4,794,195 12/1988 Hayashi et al. .................... 562/414
4,873,366 10/1989 Matsuda et al. .................... 562/416
4,990,659 2/1991 Jihad et al. ........................ 562/416

Primary Examiner—Jose G. Dees
Assistant Examiner—Vera C. Clarke
Attorney, Agent, or Firm—Oblon, Spivak, McClelland, Maier & Neustadt

[57] ABSTRACT

A process for preparing 2,6-naphthalenedicarboxylic acid comprising oxidation reaction of 2,6-diisopropylnaphthalene or an oxidation product thereof with molecular oxygen in a solvent containing an aliphatic carboxylic acid in the presence of a catalyst comprising cobalt and manganese as heavy metals and a bromine compound is disclosed, in which said oxidation reaction is carried out in the presence of at least one nitrogen-containing compound selected from the group consisting of a pyridine compound, ammonia, a carboxylic acid ammonium salt, urea, a urea derivative, an amine, and a carboxylic acid amide. 2,6-Naphthalenedicarboxylic acid can be obtained at higher purity and in increased yield.

16 Claims, No Drawings

PROCESS FOR PREPARING 2,6-NAPHTHALENEDICARBOXYLIC ACID

FIELD OF THE INVENTION

This invention relates to a process for preparing 2,6-naphthalenedicarboxylic acid and, more particularly to a process for preparing 2,6-naphthalenedicarboxylic acid which comprises oxidation reaction of 2,6-diisopropylnaphthalene or an oxidation product thereof with molecular oxygen in a solvent containing an aliphatic carboxylic acid in the presence of a catalyst composed of cobalt and manganese as heavy metals and a bromine compound.

2,6-Naphthalenedicarboxylic acid is useful as a raw material for highly functional resins such as polyethylene naphthalate (PEN).

BACKGROUND OF THE INVENTION

Among various known processes for preparing 2,6-naphthalenedicarboxylic acid, a process comprising oxidation reaction of 2,6-dimethylnaphthalene as proposed in JP-A-49-42654 (the term "JP-A" as used herein means an "unexamined published Japanese patent application") realizes reasonable yield but has difficulty in obtaining the starting material of high purity.

It has been proposed, on the other hand, to use 2,6-diisopropylnaphthalene which is relatively easy to synthesize and purify as a starting material of oxidation reaction for the production of 2,6-naphthalenedicarboxylic acid, and many proposals have been made to date to improve oxidation reactivity of this starting material.

For example, proposals so far made regarding oxidation reaction of 2,6-diisopropylnaphthalene with molecular oxygen in a solvent containing an aliphatic carboxylic acid in the presence of a catalyst comprising cobalt and manganese as heavy metals and a bromine compound include oxidation in the presence of an alkali metal (JP-A-61-246143, etc.), a salt of an inorganic acid, e.g., boric acid (JP-A-63-250344), potassium (JP-A-1-121240), cesium (JP-A-1-160943), or chlorine (JP-A-1-268661).

However, the process of using an alkali metal is attended by incorporation of the most part of the alkali metal into the reaction product in the form of a 2,6-naphthalenedicarboxylic acid salt and, therefore, requires removal of the alkali metal from the reaction product by, for example, neutralization with an inorganic acid. Besides, every time the catalyst is reused, an alkali metal must be added to the reaction system.

Further, the process of using an inorganic acid salt involves by-production of a large quantity of trimellitic acid.

SUMMARY OF THE INVENTION

An object of the present invention is to provide an industrially advantageous process for preparing 2,6-naphthalenedicarboxylic acid from 2,6-diisopropylnaphthalene, which is not accompanied by by-production of trimellitic acid or precipitation of an alkali metal salt.

The present invention provides a process for preparing 2,6-naphthalenedicarboxylic acid comprising oxidation reaction of 2,6-diisopropylnaphthalene or an oxidation product thereof with molecular oxygen in a solvent containing an aliphatic carboxylic acid in the presence of a catalyst comprising cobalt and manganese as heavy metals and a bromine compound, in which said oxidation reaction is carried out in the presence of at least one nitrogen-containing compound selected from the group consisting of a pyridine compound, ammonia, a carboxylic acid ammonium salt, urea, a urea derivative, an amine, and a carboxylic acid amide.

DETAILED DESCRIPTION OF THE INVENTION

The starting material which can be used in the present invention is 2,6-diisopropylnaphthalene or an oxidation product thereof.

The oxidation product of 2,6-diisopropylnaphthalene is an intermediary compound which is obtained by oxidation reaction of 2,6-diisopropylnaphthalene and which can be led to 2,6-naphthalenedicarboxylic acid by further oxidation reaction.

More specifically, such an oxidation product of 2,6-diisopropylnaphthalene is a 2,6-diisopropylnaphthalene derivative with its one or both of isopropyl groups being substituted with a 2-hydroperoxy-2-propyl group, 2-hydroxy-2-propyl group, an acetyl group, a formyl group, or a carboxyl group. Where both of the isopropyl groups are substituted, the two substituents may be the same or different.

Cobalt compounds and manganese compounds which can be used as catalyst components are not particularly limited and include, for example, salts with aliphatic carboxylic acids, e.g., formic acid, acetic acid, propionic acid, oxalic acid, and maleic acid; salts with alicyclic carboxylic acids, e.g., naphthenic acid; salts with aromatic carboxylic acids, e.g., benzoic acid, terephthalic acid, naphthoic acid, and naphthalenedicarboxylic acid; hydroxides; oxides; carbonates; and inorganic salts, e.g., halides. Preferred of them are cobalt acetate, cobalt bromide, manganese acetate, and manganese bromide.

The cobalt compound and the manganese compound are used as a mixture thereof at a Co:Mn atomic ratio of from 99:1 to 1:99, and preferably from 95:5 to 5:95.

Cobalt compounds and manganese compounds are used in a total amount of from 0.2 to 10% by weight, and preferably from 0.4 to 5% by weight, as the cobalt and manganese atoms based on the aliphatic carboxylic acid solvent.

The bromine compound which can be used as a catalyst component includes molecular bromine, inorganic bromine compounds, e.g., hydrogen bromide and hydrobromides, and organic bromine compounds, e.g., methyl bromide, ethyl bromide, bromoform, ethylene bromide, and bromoacetic acid.

The bromine compound is used in an amount of from 0.1 to 10 times, and preferably from 0.2 to 5 times, as the bromine atom, the total mole of cobalt and manganese atoms present in the aliphatic carboxylic acid solvent.

The aliphatic carboxylic acids which can be used as a solvent contain not more than 6 carbon atoms in the aliphatic group thereof and include formic acid, acetic acid, propionic acid, butyric acid, valeric acid, and bromoacetic acid, with acetic acid being the most preferred. These solvents may be used as diluted with other solvents such as water and aromatic hydrocarbons.

The amount of the aliphatic carboxylic acid solvent is, while not limiting, preferably ranges from 0.5 to 10 times, and more preferably from 1 to 6 times, the weight of the starting 2,6-diisopropylnaphthalene.

Molecular oxygen to be used for oxidation reaction includes pure oxygen either as it is or diluted with an inert gas, e.g., nitrogen, helium, and argon, and air. Air is enough.

In the present invention, oxidation reaction is carried out in the presence of at least one nitrogen-containing compound selected from the group consisting of a pyridine compound, ammonia, a carboxylic acid ammonium salt, urea, a urea derivative, an amine, and a carboxylic acid amide.

The pyridine compound includes unsubstituted pyridine; pyridine substituted with one to three substituents, which may be the same or different, selected from an alkyl group having from 1 to 6 carbon atoms, a hydroxyl group, an amino group, a nitro group, and a halogen atom; and pyridinium salts, N-oxides, N-alkylpyridinium halides, and addition complexes of the unsubstituted or substituted pyridine.

Specific examples of the substituted pyridine are monochloropyridine, monobromopyridine, dichloropyridine, dibromopyridine, monohydroxypyridine, dihydroxypyridine, hydroxynitropyridine, hydroxybromopyridine, aminonitropyridine, aminobromopyridine, picoline, ethylpyridine, propylpyridine, lutidine, and collidine.

The pyridinium salts include hydrochlorides, hydrobromides, chlorochromates, dichromates, p-toluenesulfonates, and sulfur trioxide salts.

The N-alkylpyridinium halides contain from 1 to 20 carbon atoms in the alkyl moiety thereof and include N-methylpyridinium chloride, N-methylpyridinium bromide, N-methylpyridinium iodide, N-ethylpyridinium chloride, N-ethylpyridinium bromide, N-ethylpyridinium iodide, N-propylpyridinium chloride, N-propylpyridinium bromide, N-propylpyridinium iodide, N-butylpyridinium chloride, N-butylpyridinium bromide, and N-butylpyridinium iodide.

The addition complexes with halogen atoms include bromopyridinium perbromide.

The ammonia includes ammonia gas and aqueous ammonia.

The carboxylic acid ammonium salts includes an ammonium salt of aliphatic carboxylic acids having from 1 to 30 carbon atoms or aromatic carboxylic acids having from 6 to 36 carbon atoms. The aliphatic group of the aliphatic carboxylic acids may be straight, branched or cyclic. Specific examples of the aliphatic carboxylic acids are mono- or dicarboxylic acids, e.g., formic acid, acetic acid, propionic acid, oxalic acid, and naphthenic acid. Specific examples of the aromatic carboxylic acids are mono- or dicarboxylic acids, e.g., benzoic acid, phthalic acid, isophthalic acid, terephthalic acid, and naphthalenedicarboxylic acid.

The urea derivatives include compounds derived from 1 to 6 molecules of urea. Specific examples of such urea derivatives are methylurea, 1,1-dimethylurea, 1,3-dimethylurea, trimethylurea, tetramethylurea, cyanuric acid, isocyanuric acid, melamine, biuret, and biurea.

The amines include aliphatic amines containing from 1 to 12 carbon atoms in the hydrocarbon moiety thereof and aromatic amines containing from 6 to 18 carbon atoms. The aliphatic group of the aliphatic amines includes an alkyl or aralkyl group having from 1 to 12 carbon atoms which may be substituted with a hydroxyl group or a carboxyl group. Examples of the alkyl group are methyl, ethyl, n-propyl, isopropyl, n-butyl, isobutyl, t-butyl, 1-methylpropyl, cyclohexyl, n-octyl, hydroxyethyl, and carboxymethyl groups.

Specific examples of the aliphatic amines are methylamine, dimethylamine, trimethylamine, ethylamine, diethylamine, triethylamine, n-propylamine, di-n-propylamine, tri-n-propylamine, isopropylamine, diisopropylamine, triisopropylamine, n-butylamine, di-n-butylamine, tri-n-butylamine, i-butylamine, diisobutylamine, triisobutylamine, t-butylamine, di-t-butylamine, tri-t-butylamine, cyclohexylamine, dicyclohexylamine, tricyclohexylamine, n-octylamine, di-n-octylamine, tri-n-octylamine, ethylenediamine, 1,2-diaminopropane, 1,3-diaminopropane, N-methylethylenediamine, N,N-dimethylethylenediamine, N,N'-dimethylethylenediamine, N,N,N'-trimethylethylenediamine, N,N,N',N'-tetramethylethylenediamine, N-methyl-1,2-diaminopropane, N-methyl-1,3-diaminopropane, N,N-dimethyl-1,2-diaminopropane, N,N-dimethyl-1,3-diaminopropane, N,N,N'-trimethyl-1,2-diaminopropane, N,N,N'-trimethyl-1,3-diaminopropane, N,N,N',N'-tetramethyl-1,2-diaminopropane, N,N,N',N'-tetramethyl-1,3-diaminopropane, monoethanolamine, diethanolamine, triethanolamine, glycine, piperidine, N-methylpiperidine, hexamethyleneimine, N-methylhexamethyleneimine, ethylenediaminetetraacetic acid and metal salts thereof, diethylenetriaminepentaacetic acid and metal salts thereof, glycol ether diaminetetraacetic acid and metal salts thereof, 1,2-diaminopropanetetraacetic acid and metal salts thereof, and trans-1,2-cyclohexanediaminetetraacetic acid and metal salts thereof.

Specific examples of the aromatic amines are aniline, N-methylaniline, N,N-dimethylaniline, o-, m- or p-toluidine, N-methyl-o-, m- or p-toluidine, N,N-dimethyl-o-, m- or p-toluidine, benzylamine, N-methylbenzylamine, and N,N-dimethylbenzylamine.

The carboxylic acid amides include aliphatic carboxylic acid amides containing from 1 to 30 carbon atoms and aromatic carboxylic acid amides containing from 6 to 36 carbon atoms.

Specific examples of the aliphatic carboxylic acid amides are formamide, N,N-dimethylformamide (DMF), N,N-diethylformamide, acetamide, N,N-dimethylacetamide (DMAc), N,N-diethylacetamide, malonamide, N,N,N',N'-tetramethylmalonamide, and N,N,N',N'-tetraethylmalonamide.

Specific examples of the aromatic carboxylic acid amides are benzamide, N,N-dimethylbenzamide, N,N-diethylbenzamide, 2-naphthylamide, N,N-dimethyl-2-naphthylbenzamide, N,N-diethyl-2-naphthylbenzamide, terephthaldiamide, N,N,N',N'-tetramethylterephthaldiamide, N,N,N',N'-tetraethylterephthaldiamide, 2,6-naphthalenediamide, N,N,N',N'-tetramethyl-2,6-naphthalenediamide, and N,N,N',N'-tetraethyl-2,6-naphthalenediamide.

The above-described nitrogen-containing compounds may be used either individually or as a mixture of two or more thereof at an arbitrary mixing ratio.

The nitrogen-containing compounds are used in a total amount of from 0.01 to 50 mols, and preferably from 0.05 to 20 mols, per mol of the bromine atom added to the reaction system. In using a pyridine compound in particular, it is used in an amount of from 0.1 to 50 mols, and preferably from 0.5 to 20 mols, per mol of the bromine atom.

The reaction can be carried out in any of a batch system, a semi-batch system, and a continuous system. A semi-batch system is usually adopted.

In cases where the reaction is effected in a semi-batch system, a solvent and a catalyst system are charged in a reaction apparatus, and 2,6-diisopropylnaphthalene in a molten state is continuously fed thereto under a prescribed temperature and pressure condition while blowing molecular oxygen-containing gas. After a prescribed amount of 2,6-diisopropylnaphthalene is fed, blowing of oxygen-containing gas is further continued for a given period of time. The optimum feed rate of 2,6-diisopropylnaphthalene cannot be specified as it depends on the reaction temperature, the reaction pressure, and the amount of the catalyst. Usually, the whole amount of 2,6-diisopropylnaphthalene is fed in 1 to 12 hours.

Where the reaction is performed in a batch system, a solvent, a catalyst, and 2,6-diisopropylnaphthalene are charged in a reaction apparatus, and oxygen-containing gas is blown thereinto at a prescribed temperature for a prescribed period of time.

The reaction temperature usually ranges from 100° to 300° C., and preferably from 150° to 250° C. Too a low temperature considerably reduces the reaction rate, and too a high temperature increases losses of the solvent and the starting material due to combustion.

The reaction pressure, though not critical, is preferably set so that the oxygen partial pressure in the gaseous phase is from 0.2 to 10 kg/cm$^2$-absolute taking the reaction rate into consideration.

The thus produced 2,6-naphthalenedicarboxylic acid is scarcely soluble in the aliphatic carboxylic acid solvent and precipitated in the reaction mixture. In the case of a semi-batchwise reaction, the reaction mixture is cooled, and the precipitate is collected by filtration.

Since the aliphatic carboxylic acid solvent separated by filtration has dissolved therein the most part of the catalyst and the reaction intermediates, it can be repeatedly reused. For reuse, a catalyst, a solvent and a nitrogen-containing compound are added, if necessary, to the recovered solvent to make up for the loss due to, for example, adhesion to the produced 2,6-naphthalenedicarboxylic acid.

According to the process of the present invention, a yield is increased without increasing the amount of a catalyst, and high purity 2,6-naphthalenedicarboxylic acid can effectively be produced from 2,6-diisopropylnaphthalene without being accompanied by precipitation of an alkali metal salt of 2,6-dinaphthalenedicarboxylic acid in the reaction product.

The present invention is now illustrated in greater detail by way of Examples, but it should be understood that the present invention is not deemed to be limited thereto. All the yields are given by mol% based on the starting 2,6-diisopropylnaphthalene. The purity of 2,6-naphthalenedicarboxylic acid produced was determined by high performance liquid chromatography, expressed in percent area at UV 285 nm.

EXAMPLE 1

In a 500 ml titanium-made autoclave equipped with a reflux condenser, a gas introducing pipe, a feed pump for a starting material, a back-pressure regulator, and an induction stirrer were charged 200 g of acetic acid, 9.35 g (37.5 mmol) of cobalt acetate tetrahydrate, 9.20 g (37.5 mmol) of manganese acetate tetrahydrate, 7.35 g (75.0 mmol) of ammonium bromide, and 5.93 g (75.0 mmol) of pyridine. After displacing the atmosphere with nitrogen, the inner pressure was adjusted to 30 kg/cm$^2$G with the back-pressure regulator. The inner temperature was raised to 200° C., and air was fed therein at a rate of 3 to 4 Nl/min to keep the inner pressure at 30 kg/cm$^2$G (oxygen partial pressure: 6.5 kg/cm$^2$).

After the system became stable, 79.62 g (375 mmol) of 2,6-diisopropylnaphthalene was continuously fed over 4 hours. After completion of the feeding, air feeding was further continued for 1 hour while maintaining the system at 200° C. and 30 kg/cm$^2$G.

After completion of the reaction, the reaction mixture was cooled to room temperature, and the precipitated solid was collected by filtration and washed with 40 g of acetic acid. The filtration mother liquor and the washing totaled to 254.4 g. The collected solid was dried to obtain 67.2 g of a pale brown solid. The purity of the resulting crude 2,6-naphthalenedicarboxylic acid was 99.4%, and the yield was 82.4%.

EXAMPLE 2

In the same reaction apparatus as used in Example 1 were charged 200 g of acetic acid, 6.23 g (25.0 mmol) of cobalt acetate tetrahydrate, 6.13 g (25.0 mmol) of manganese acetate tetrahydrate, 4.90 g (50.0 mmol) of ammonium bromide, and 7.90 g (100.0 mmol) of pyridine, the reaction atmosphere displaced with nitrogen, and the inner pressure adjusted to 30 kg/cm$^2$G with the back-pressure regulator. The content was heated to 200° C., and air was fed thereinto at a rate of 3 to 4 Nl/min to keep the inner pressure at 30 kg/cm$^2$G (oxygen partial pressure 6.5 kg/cm$^2$).

After the system became stable, 79.62 g (375 mmol) of 2,6-diisopropylnaphthalene was continuously fed over 4 hours. After completion of the feeding, air feeding was further continued for 1 hour while keeping the system at 200° C. and 30 kg/cm$^2$G.

After completion of the reaction, the autoclave was cooled to room temperature, and the precipitated solid was collected by filtration and washed with 40 g of acetic acid. The filtration mother liquor and the washing totaled to 236.6 g. The collected solid was dried to obtain 64.5 g (yield: 80.3%) of a pale brown crude 2,6-naphthalenedicarboxylic acid having a purity of 99.1%.

COMPARATIVE EXAMPLE 1

The same procedures as in Example 1 were repeated, except that no pyridine was used, to obtain 56.1 g (yield: 57.8%) of a brown crude 2,6-naphthalenedicarboxylic acid having a purity of 97.1%.

COMPARATIVE EXAMPLE 2

In the same reaction apparatus as used in Example 1 were charged 200 g of acetic acid, 9.35 g (37.5 mmol) of cobalt acetate tetrahydrate, 9.20 g (37.5 mmol) of manganese acetate tetrahydrate, 8.93 g (75.0 mmol) of potassium bromide, and 7.37 g (75.0 mmol) of potassium acetate, the reaction atmosphere displaced with nitrogen, and the inner pressure adjusted to 30 kg/cm$^2$G with the back-pressure regulator. The content was heated to 200° C., and air was fed thereinto at a rate of 3 to 4 Nl/min to keep the inner pressure at 30 kg/cm$^2$G (oxygen partial pressure: 6.5 kg/cm$^2$).

After the system became stable, 79.62 g (375 mmol) of 2,6-diisopropylnaphthalene was continuously fed over 4 hours. After completion of the feeding, air feeding was further continued for 1 hour while keeping the system at 210° C. and 30 kg/cm$^2$G.

After completion of the reaction, the autoclave was cooled to room temperature, and the precipitated solid was collected by filtration and washed with 40 g of acetic acid. The filtration mother liquor and the washing totaled to 148.6 g. The collected solid was dried to obtain 68.2 g of a pale brown solid.

The resulting product was found to contain 22.0 g of potassium 2,6-naphthalenedicarboxylate. The crude product was then washed with dilute hydrochloric acid, washed with water, and dried to obtain 65.1 g of a pale brown solid. The resulting crude 2,6-naphthalenedicarboxylic acid had a purity of 99.6%, and the yield was 80.0%.

EXAMPLE 3

The same procedures as in Example 1 were repeated, except for replacing pyridine with 4.50 g (75.0 mmol) of urea and changing the air feed rate to 5 Nl/min. The oxygen partial pressure in the reaction system was 4.5 kg/cm$^2$.

After completion of the reaction, the autoclave was cooled to room temperature, and the precipitated solid was collected by filtration and washed with 30 g of acetic acid. The filtration mother liquor and the washing totaled to 187.2 g. The collected solid was dried to obtain 64.3 g (yield: 79.0%) of a pale brown crude 2,6-naphthalenedicarboxylic acid having a purity of 99.6%.

EXAMPLE 4

The same procedures as in Example 3 were repeated, except for replacing urea with 4.84 g (37.5 mmol) of cyanuric acid. The oxygen partial pressure in the reaction system was 4.5 kg/cm$^2$.

After completion of the reaction, the autoclave was cooled to room temperature, and the precipitated solid was collected by filtration and washed with 30 g of acetic acid. The filtration mother liquor and the washing totaled to 246.3 g. The collected solid was dried to obtain 65.2 g (yield: 77.6%) of a brown crude 2,6-naphthalenedicarboxylic acid having a purity of 96.5%.

EXAMPLE 5

The same procedures as in Example 3 were repeated, except for replacing urea with 4.38 g (15.0 mmol) of ethylenediaminetetraacetic acid. The oxygen partial pressure in the reaction system was 4.5 kg/cm$^2$.

After completion of the reaction, the autoclave was cooled to room temperature, and the precipitated solid was collected by filtration and washed with 40 g of acetic acid. The filtration mother liquor and the washing totaled to 272.0 g. The collected solid was dried to obtain 64.3 g (yield: 79.1%) of a pale brown crude 2,6-naphthalenedicarboxylic acid having a purity of 96.7%.

EXAMPLE 6

The same procedures as in Example 3 were repeated, except for replacing urea with 5.10 g (75.0 mmol) of 25 wt % aqueous ammonia and changing the reaction time after feeding the starting material to 30 minutes. The oxygen partial pressure in the reaction system was 4.5 kg/cm$^2$.

After completion of the reaction, the autoclave was cooled to room temperature, and the precipitated solid was collected by filtration and washed with 40 g of acetic acid. The filtration mother liquor and the washing totaled to 213.2 g. The collected solid was dried to obtain 66.5 g of a pale brown solid. The resulting crude 2,6-naphthalenedicarboxylic acid had a purity of 97.4% and was confirmed to contain no ammonium salt by infrared spectroscopic analysis. The yield was 80.0%.

EXAMPLE 7

The same procedures as in Example 3 were repeated, except for replacing urea with 5.78 g (75 mmol) of ammonium acetate and changing the reaction time after feeding the starting material to 30 minutes. The oxygen partial pressure in the reaction system was 4.5 kg/cm$^2$.

After completion of the reaction, the autoclave was cooled to room temperature, and the precipitated solid was collected by filtration and washed with 40 g of acetic acid. The filtration mother liquor and the washing totaled to 254.1 g. The collected solid was dried to obtain 66.6 g of a pale brown solid. The resulting crude 2,6-naphthalenedicarboxylic acid had a purity of 98.8% and was confirmed to contain no ammonium salt by infrared spectroscopic analysis. The yield was 81.2%.

EXAMPLE 8

The same procedures as in Example 3 were repeated, except for replacing urea with 5.48 g (75.0 mmol) of DMF and changing the reaction pressure to 25 kg/cm$^2$G. The oxygen partial pressure in the reaction system was 4.5 kg/cm$^2$.

After completion of the reaction, the autoclave was cooled to room temperature, and the precipitated solid was collected by filtration and washed with 40 g of acetic acid. The filtration mother liquor and the washing totaled to 254.3 g. The collected solid was dried to obtain 60.1 g of a pale brown solid. The resulting crude 2,6-naphthalenedicarboxylic acid had a purity of 98.3% and was confirmed to contain no ammonium salt by infrared spectroscopic analysis. The yield was 74.1%.

EXAMPLE 9

The same procedures as in Example 3 were repeated, except for replacing urea with 6.53 g (75.0 mmol) of DMAc and changing the reaction pressure to 25 kg/cm$^2$G. The oxygen partial pressure in the reaction system was 4.5 kg/cm$^2$.

After completion of the reaction, the autoclave was cooled to room temperature, and the precipitated solid was collected by filtration and washed with 40 g of acetic acid. The filtration mother liquor and the washing totaled to 207.6 g. The collected solid was dried to obtain 54.9 g of a pale brown solid. The resulting crude 2,6-naphthalenedicarboxylic acid had a purity of 97.7% and was confirmed to contain no ammonium salt by infrared spectroscopic analysis. The yield was 66.0%.

EXAMPLE 10

The same procedures as in Example 3 were repeated, except for replacing urea with 4.58 g (75.0 mmol) of monoethanolamine and changing the reaction time after feeding the starting material to 30 minutes. The oxygen partial pressure in the reaction system was 4.5 kg/cm$^2$.

After completion of the reaction, the autoclave was cooled to room temperature, and the precipitated solid was collected by filtration and washed with 40 g of acetic acid. The filtration mother liquor and the washing totaled to 235.9 g. The collected solid was dried to obtain 61.4 g of a pale brown solid. The resulting crude 2,6-naphthalenedicarboxylic acid had a purity of 98.4% and was confirmed to contain no ammonium salt by infrared spectroscopic analysis. The yield was 74.5%.

EXAMPLE 11

The same procedures as in Example 3 were repeated, except for replacing urea with 2.25 g (37.5 mmol) of ethylenediamine and changing the reaction time after feeding the starting material to 30 minutes. The oxygen partial pressure in the reaction system was 4.5 kg/cm².

After completion of the reaction, the autoclave was cooled to room temperature, and the precipitated solid was collected by filtration and washed with 40 g of acetic acid. The filtration mother liquor and the washing totaled to 201.2 g. The collected solid was dried to obtain 57.1 g of a pale brown solid. The resulting crude 2,6-naphthalenedicarboxylic acid had a purity of 98.9% and was confirmed to contain no ammonium salt by infrared spectroscopic analysis. The yield was 68.9%.

EXAMPLE 12

The same procedures as in Example 3 were repeated, except for replacing urea with 7.59 g (37.5 mmol) of triethylamine and changing the reaction time after feeding the starting material to 30 minutes. The oxygen partial pressure in the reaction system was 4.5 kg/cm².

After completion of the reaction, the autoclave was cooled to room temperature, and the precipitated solid was collected by filtration and washed with 40 g of acetic acid. The filtration mother liquor and the washing totaled to 264.1 g. The collected solid was dried to obtain 59.3 g of a pale brown solid. The resulting crude 2,6-naphthalenedicarboxylic acid had a purity of 97.4% and was confirmed to contain no ammonium salt by infrared spectroscopic analysis. The yield was 69.3%.

EXAMPLE 13

The same procedures as in Example 3 were repeated, except for replacing urea with 6.39 g (75 mmol) of piperidine and changing the reaction time after feeding the starting material to 30 minutes. The oxygen partial pressure in the reaction system was 4.5 kg/cm².

After completion of the reaction, the autoclave was cooled to room temperature, and the precipitated solid was collected by filtration and washed with 40 g of acetic acid. The filtration mother liquor and the washing totaled to 220.3 g. The collected solid was dried to obtain 64.8 g of a pale brown solid. The resulting crude 2,6-naphthalenedicarboxylic acid had a purity of 98.6% and was confirmed to contain no ammonium salt by infrared spectroscopic analysis. The yield was 78.8%.

While the invention has been described in detail and with reference to specific examples thereof, it will be apparent to one skilled in the art that various changes and modifications can be made therein without departing from the spirit and scope thereof.

What is claimed is:

1. A process for preparing 2,6-naphthalenedicarboxylic acid, comprising
   oxidizing 2,6-diisopropylnaphthalene or an oxidation product thereof with molecular oxygen in a solvent containing an aliphatic carboxylic acid in the presence of a catalyst comprising cobalt and manganese as heavy metals, wherein the cobalt:manganese atomic ratio is from 99:1 to 1:99, and cobalt and manganese are present in a total amount of from 0.2 to 10% by weight based on the aliphatic carboxylic acid solvent, and a bromine compound, wherein said bromine compound is present in an amount from 0.1 to 10 times, as the bromine atom, the total moles of cobalt and manganese atoms, in which said oxidizing reaction is carried out at a temperature from 100° to 300° C. and an oxygen partial pressure in the gaseous phase of from 0.2 to 10 kg/cm²-absolute in the presence of 0.01 to 50 mol % based on the bromine atoms of at least one nitrogen-containing compound selected from the group consisting of a pyridine compound, ammonia, a carboxylic acid ammonium salt, urea, a urea derivative, an amine, and a carboxylic acid amide.

2. A process as claimed in claim 1, wherein said pyridine compound is unsubstituted pyridine; pyridine substituted with one to three substituents, which may be the same or different, selected from the group consisting of an alkyl group having from 1 to 6 carbon atoms, a hydroxyl group, an amino group, a nitro group, and a halogen atom; a pyridinium salt thereof, an N-oxide thereof, an N-alkylpyridinium halide thereof having from 1 to 20 carbon atoms in the alkyl moiety, and an addition complex thereof.

3. A process as claimed in claim 1, wherein said carboxylic acid ammonium salt is an ammonium salt of an aliphatic carboxylic acid having from 1 to 30 carbon atoms or an aromatic carboxylic acid having from 6 to 36 carbon atoms.

4. A process as claimed in claim 1, wherein said urea derivative is a compound derived from 1 to 6 molecules of urea.

5. A process as claimed in claim 1, wherein said amine is an aliphatic amine containing from 1 to 12 carbon atoms in the hydrocarbon moiety thereof or an aromatic amine containing from 6 to 18 carbon atoms.

6. A process as claimed in claim 1, wherein said carboxylic acid amide is an aliphatic carboxylic acid amide containing from 1 to 30 carbon atoms or an aromatic carboxylic acid amide containing from 6 to 36 carbon atoms.

7. A process as claimed in claim 1, wherein said cobalt is used as cobalt acetate or cobalt bromide.

8. A process as claimed in claim 1, wherein said manganese is used as manganese acetate or manganese bromide.

9. A process as claimed in claim 1, wherein said aliphatic carboxylic acid contains not more than 6 carbon atoms in the aliphatic group thereof.

10. A process as claimed in claim 1, wherein said aliphatic carboxylic acid solvent is present in an amount of from 0.5 to 10 times the weight of the 2,6-diisopropylnaphthalene.

11. A process as claimed in claim 1, wherein the cobalt:manganese atomic ratio is from 95:5 to 5:95.

12. A process as claimed in claim 1, wherein cobalt and manganese are present in a total amount of from 0.4 to 5% by weight based on the aliphatic carboxylic acid solvent.

13. A process as claimed in claim 1, wherein said bromine compound is present in an amount of from 0.2 to 5 times, as the bromine atom, the total moles of cobalt and manganese atoms.

14. A process as claimed in claim 1, wherein said aliphatic carboxylic acid solvent is present in an amount of from 1 to 6 times the weight of the 2,6-diisopropylnaphthalene.

15. A process as claimed in claim 1, wherein said nitrogen-containing compound is present in a total amount of from 0.05 to 20 mol % based on the bromine atoms.

16. A process as claimed in claim 1, wherein said oxidizing reaction is at a temperature of from 150° to 250° C.

* * * * *